United States Patent [19]

Rodomista et al.

[11] Patent Number: 4,932,629

[45] Date of Patent: Jun. 12, 1990

[54] CLAMP FOR FLEXIBLE TUBING

[75] Inventors: Guy F. Rodomista, Natick; Michael J. Monahan, Needham; Arthur L. Malenfant, Cambridge, all of Mass.

[73] Assignee: Nova Biomedical Corporation, Waltham, Mass.

[21] Appl. No.: 408,540

[22] Filed: Sep. 18, 1989

[51] Int. Cl.⁵ .............................................. F16K 7/02
[52] U.S. Cl. .......................................... 251/4; 251/7
[58] Field of Search ........................................ 251/4, 7

[56] References Cited

U.S. PATENT DOCUMENTS 3,316,935  5/1967  Kaiser et al. ........................ 251/4 X
3,357,674 12/1967  Coanda et al. .......................... 251/7
3,374,509  3/1968  Logan et al. ........................ 251/4 X
4,248,401  2/1981  Mittleman .............................. 251/7

Primary Examiner—John C. Fox

[57] ABSTRACT

A clamping device for controlling liquid flow in a length of flexible tubing; the device includes a generally planar support having a keyhole, an annular flexible sleeve seated in the keyhole for receiving the tubing in an orientation generally perpendicular to the planar support, and a mechanism for moving the flexible sleeve between the larger side of the keyhole and the smaller side of the keyhole to cause pinching of the tubing to control liquid flow.

7 Claims, 3 Drawing Sheets

CLAMP FOR FLEXIBLE TUBING

BACKGROUND OF THE INVENTION

This invention relates to clamps to control liquid flow in flexible tubing.

In laboratory equipment which uses flexible tubing to dispense liquid reagents, for example, the operator may need to temporarily stop the flow of the liquid. Typical clamps pinch the tubing either with a scissors like action or by forcing the tubing into a space which deforms it.

SUMMARY OF THE INVENTION

In general, the invention features a clamping device for controlling liquid flow in a length of flexible tubing; the device includes a generally planar support having a keyhole, an annular flexible sleeve seated in the keyhole for receiving the tubing in an orientation generally perpendicular to the planar support, and a mechanism for moving the flexible sleeve between the larger side of the keyhole and the smaller side of the keyhole to cause pinching of the tubing to control liquid flow.

Preferred embodiments include the following features. The smaller side of the keyhole is small enough to fully stop the liquid flow when the tubing and sleeve are received in the smaller side. The mechanism for moving the sleeve includes a holder housed in and slidable transversely relative to the support. The keyhole has a stepped perimeter wall for housing the sleeve. The sleeve is an "o"-ring and is formed of an elastomeric material, preferably rubber. The support includes multiple keyholes each serving a corresponding length of flexible tubing.

The clamp is easily manufactured and used, and the sleeve reduces wear and tear on the tubing. To the extent that wear occurs, the elastomeric nature of the sleeve allows it to accommodate thinning of the tubing that may have occurred.

Other features and advantages of the invention will become apparent from the following description of the preferred embodiment and from the claims.

DESCRIPTION OF THE PREFERRED EMBODIMENT

We first briefly describe the drawings.

Drawings

Structure

Figure 1:
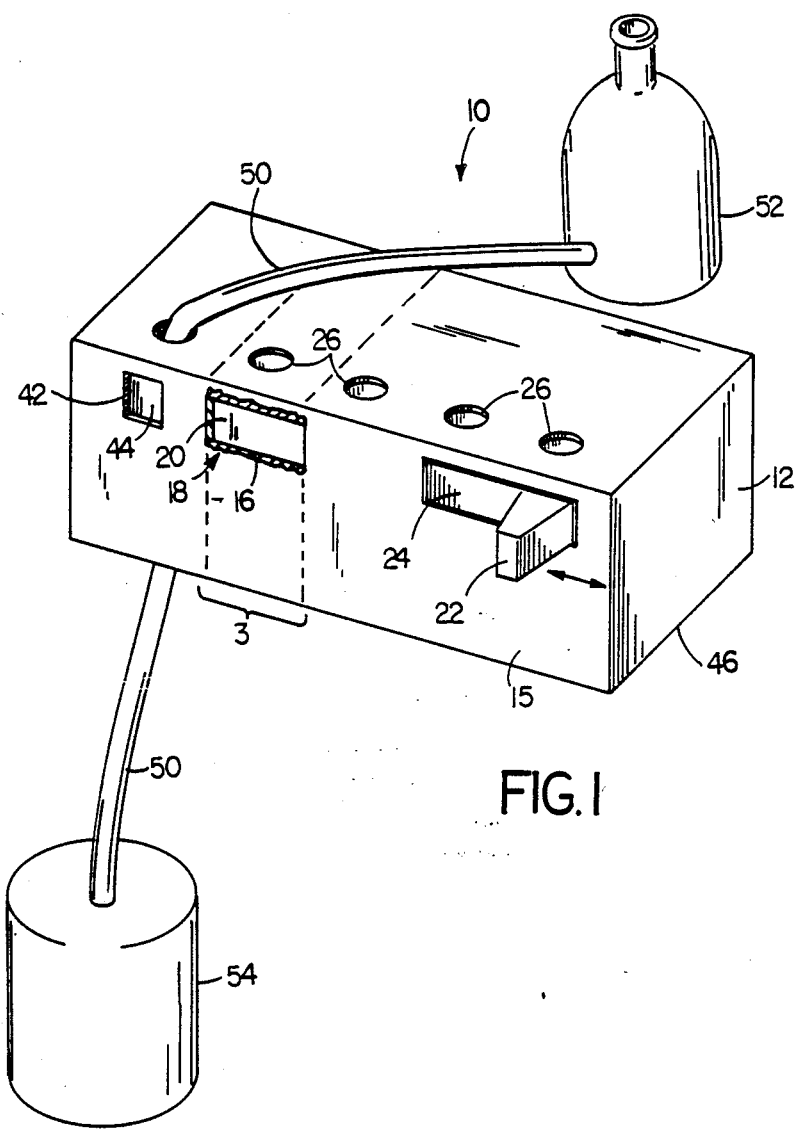
FIG. 1 is a perspective view, partially cut away, of a clamping device.

Referring to FIG. 1, flexible polyvinyl chloride TygonT tubing 50 carries a reagent from a dispensing reservoir 52 to a chemical analyzer 54. To control the flow of reagent in tubing 50, the tubing is held in a clamping device 10.

Figure 2:
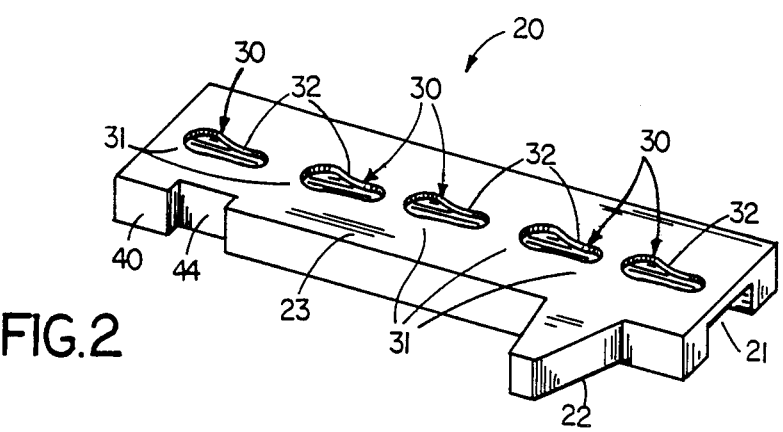
FIG. 2 is a perspective view of the slide bar of the clamp.

Referring also to FIG. 2, clamping device 10 includes a black plastic slide bar 20 held in a housing 12. A row of five keyholes 30 are cut through the slide bar and open into a channel 21. The large end of each keyhole has a generally circular opening 31 (diameter 0.201") which connects to a smaller oval opening 32 (generally 0.150"×0.096").

Figure 4:
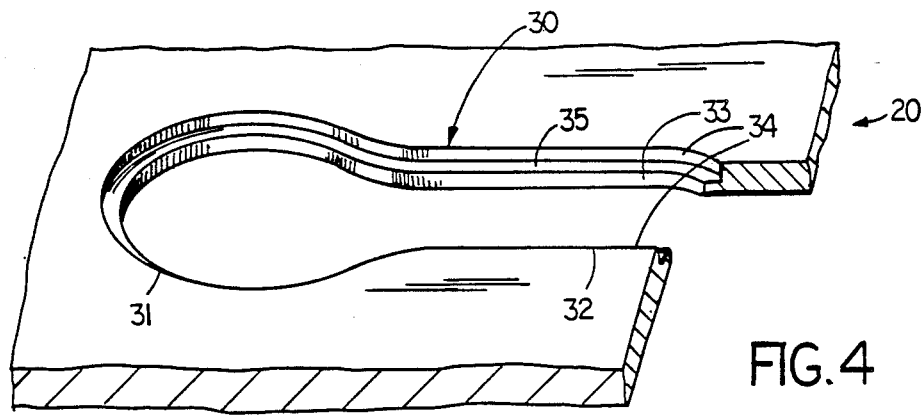
FIG. 4 is a perspective view, partially cut away, of one keyhole channel in the slide bar.
Figure 5:
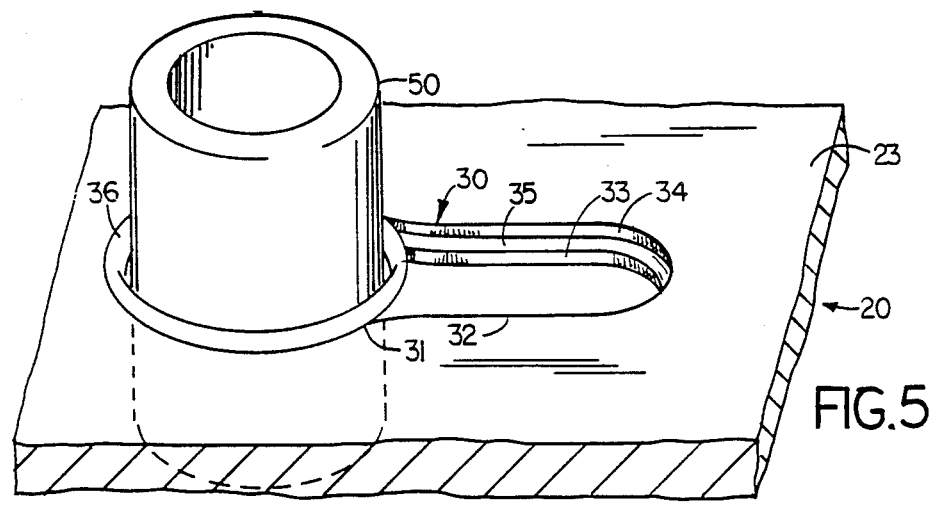
FIGS. 5 and 6 are perspective views like FIG. 4 with tubing in the keyhole channel, in two different positions respectively.
Figure 6:
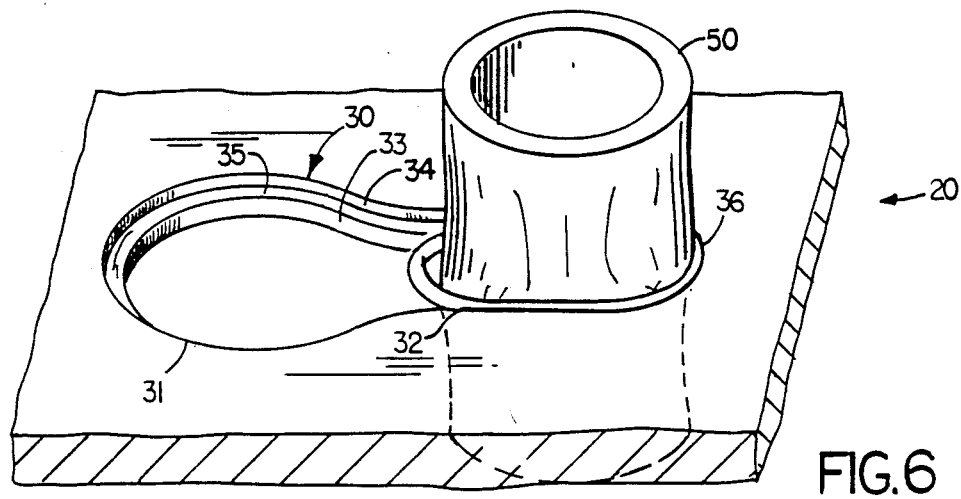

Referring also to FIG. 4, the border of each keyhole is stepped. The two vertical walls 33, 34 defining step 35 have the same contours and the same alignment. Inner wall 33 is slightly smaller than outer wall 34. Step 34 houses a rubber "o"-ring (sleeve) 36 (FIG. 5) in a position flush with the surface 23 of slide bar 20.

Referring again to FIG. 2, a lever 22 protrudes from one end of the long edge of slide bar 20, and a red indicator square 44 is recessed slightly at the other end, next to black area 40.

Figure 3:
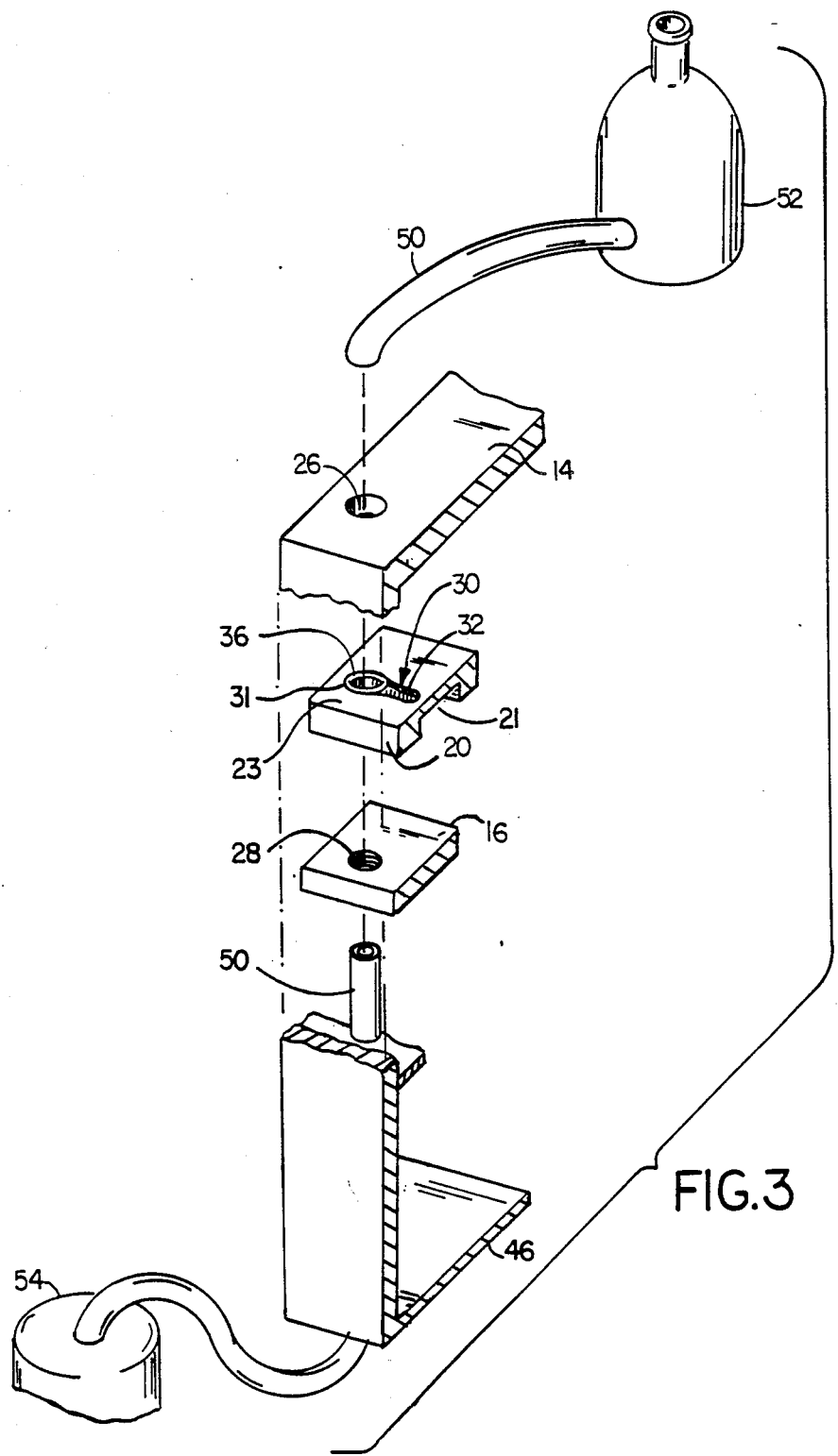
FIG. 3 is an exploded perspective view, not to scale, of segment 3 of the clamp of FIG. 1.

Referring also to FIG. 3, slide bar 20 is seated snugly in a slot 18 molded between upper 14 and lower 16 portions of housing 12. Lever 22 extends through an opening 24 (twice as wide as lever 22) in housing wall 15. A row of five holes 26 in the upper portion 14 of the housing, spaced approximately 0.5" apart on center, is aligned with a similar row of five holes 28 in lower portion 16. Thus five different sections of flexible tubing can be accommodated.

When lever 22 of slide bar 20 is in the "open" position on the right side of opening 24 (and black area 40 of slide bar 20 shows through window 42), the larger portions 31 of keyholes 30 in slide bar 20 are aligned with holes 26, 28 in the upper 14 and lower 16 portions of housing 12 (FIG. 3). When lever 22 is pushed to the left side, "closed" position (and red area 44 on slide bar 20 shows through window 42), the smaller portions 32 of keyholes 30 are aligned with the holes 26, 28 in the upper 14 and lower 16 portions of the housing 12.

Operation

Tubing 50 is inserted through top housing hole 26, through rubber "o"-ring 36 temporarily seated in larger portion 31 of keyhole 30 in slide bar 20, and through the corresponding lower housing hole 28. With the slide bar 20 aligned in the open position (lever 22 to the right), liquid will flow freely through tubing 50. When the slide bar lever 22 is pushed to the left, the upper and lower housing holes 26, 28 hold each piece of tubing 50 securely, and the tubing 50 and its surrounding "o" ring 36 are forced into smaller portion 32 of keyhole 30, thus distorting tubing 50 and pinching its sides together so as to cut off the flow of liquid. Part of the distorted "o"-ring 36 protrudes back out of smaller portion 32 into larger portion 31.

The "o"-ring cushions the tubing when it is forced into the smaller portion of the keyhole, saving wear and tear on the tubing. The elastomeric properties of the "o"-ring allow the clamp to accommodate wear and tear and associated thinning of the tubing that may occur.

Other embodiments are within the following claims.

We claim:

1. A clamping device for controlling liquid flow in a length of flexible tubing comprising
    a generally planar support having a keyhole,
    an annular, flexible sleeve seated in said keyhole for receiving said tubing in an orientation generally perpendicular to said planar support, and
    a mechanism for moving said flexible sleeve between the larger side of the keyhole and the smaller side of the keyhole to cause pinching of said tubing to control liquid flow in the tubing.

2. The clamp of claim 1 wherein said smaller side of said keyhole is small enough to fully stop said liquid flow when said tubing and sleeve are received in said smaller side.

3. The clamp of claim 1 wherein said mechanism comprises a holder for holding said tubing, said holder being housed in and slidable transversely relative to said support.

4. The clamp of claim 1 wherein said keyhole has a stepped perimeter wall for housing said sleeve.

5. The clamp of claim 1 wherein said sleeve comprises an "o" ring.

6. The clamp of claim 1 wherein said clamp is formed of an elastomeric material, preferably rubber.

7. The clamp of claim 1 wherein said support comprises multiple keyholes each serving a corresponding length of flexible tubing.

* * * * *